United States Patent [19]

Kuroda et al.

[11] 4,357,690
[45] Nov. 2, 1982

[54] SWITCH CIRCUIT FOR EXCITING ULTRASONIC TRANSDUCER ELEMENTS

[75] Inventors: Masao Kuroda, Tokyo; Sekijyuro Ono, Ooita; Toshio Kondo, Kunitachi; Noriyoshi Ichikawa, Nara, all of Japan

[73] Assignee: Hitachi Medical Corporation, Tokyo, Japan

[21] Appl. No.: 217,022

[22] Filed: Dec. 16, 1980

[30] Foreign Application Priority Data

Dec. 24, 1979 [JP] Japan ................................ 54-166875

[51] Int. Cl.³ ............................................. G01S 7/52
[52] U.S. Cl. ..................................... 367/8.7; 310/317; 310/318; 367/105; 367/137; 367/903
[58] Field of Search ................ 367/137, 903, 87, 105; 310/317, 318; 307/256, 259

[56] References Cited

U.S. PATENT DOCUMENTS

| | | | |
|---|---|---|---|
| 2,823,321 | 2/1958 | Sims, Jr. | 307/256 |
| 3,102,991 | 9/1963 | Jess | 367/87 |
| 3,117,241 | 1/1964 | Paynter et al. | 367/903 X |

*Primary Examiner*—Richard A. Farley
*Attorney, Agent, or Firm*—Antonelli, Terry & Wands

[57] ABSTRACT

A circuit for exciting an ultrasonic transducer element comprises a diode switch exhibiting a long reverse recovery time duration connected between an input and an output terminal. A transducer exciting signal varying in both positive and negative directions and applied to the input terminal is conducted to the output terminal through the diode switch.

9 Claims, 16 Drawing Figures

TO ECHO PROCESSORS

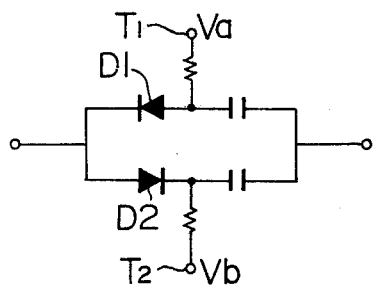
FIG. 3 PRIOR ART
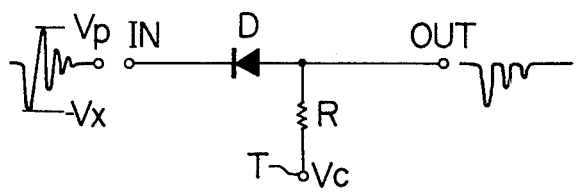
FIG. 4a PRIOR ART  FIG. 4b PRIOR ART  FIG. 4c PRIOR ART
FIG. 5
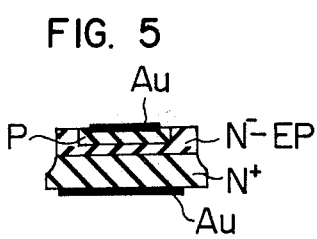
FIG. 6
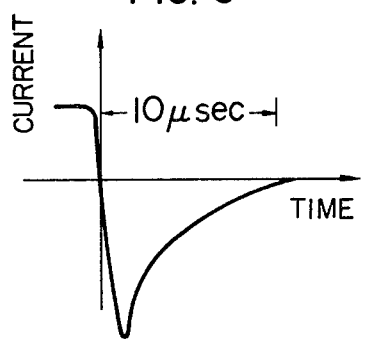

SWITCH CIRCUIT FOR EXCITING ULTRASONIC TRANSDUCER ELEMENTS

BACKGROUND OF THE INVENTION

The present invention relates to an excitation circuit for exciting ultrasonic transducer elements.

Recently, there has been developed an ultrasonic diagnostic apparatus of electronic scanning type in which use is made of a probe composed of a plurality of strip-like ultrasonic transducer elements disposed in an array. For having a better understanding of the invention, description will first be made in some detail on the principle of the ultrasonic diagnostic apparatus of linear scan type among those of the electronic scanning type. Referring to FIG. 1, k transducer elements 1 (hereinafter referred to also as element) which are simultaneously excited are grouped into one set, where k is equal to 4 in the case of the illustrated example. The excitation of the transducer elements grouped in one set is then sequentially changed over from one to another succeeding element on the one-by-one basis so that the ultrasonic beams produced by the selectively grouped elements to be excited simultaneously are shifted progressively in the direction in which the transducer elements are arrayed in a linear row. In other words, the ultrasonic beams are sequentially emitted in a linear order, as indicated by scanning lines $L_1, L_2, \ldots, L_{n-4+1}$ in FIG. 1. By the way, when the number of all the transducer elements 1 is represented by n, the total number M of the scanning by the ultrasonic beams can be expressed by $n-k+1$, where k represents the number of the transducer elements excited simultaneously, as defined above. Assuming that $n=100$ and $k=4$, a first scanning line $L_1$ is obtained by driving pulsers $P_1$ to $P_4$ connected to the transducer elements #1 to #4. A second scanning line $L_2$ is produced by driving the pulsers $P_2$ to $P_5$ connected to the elements #2 to #5. By repeating sequentially the driving of the pulsers in the similar manner, 97 scanning lines can be obtained in total along the transducer element array. Under the circumstance, when the number of the scanning lines is to be increased, a correspondingly increased number of pulsers are required, which of course means high expensiveness of the scanner or probe. Accordingly, in the practical applications, a switching circuit is employed with a view to decreasing the number of the pulsers to a possible minimum. FIG. 2 shows an arrangement including a switching circuit to this end. Referring to the figure, the transducer elements 1 and the pulsers $P_1$ to $P_4$ are interconnected through a matrix-like switching circuit in which the individual switches $S_1$ to $S_4$, $S_5$ to $S_9$, ..., $S_{n-3}$ to $S_n$ are provided at the cross-points between the lines outgoing from the pulsers and the lines leading to the transducer elements for every group of the elements. It will be seen that the arrangement shown in FIG. 2 allows the number of the pulser P to be decreased to that of the elements excited simultaneously at minimum. In this connection, it should however be mentioned that the pulse voltage produced by the pulser for exciting the transducer element which is generally a piezo-electric type in the case of the ultrasonic diagnostic apparatus is usually in a form of a burst waveform signal of about peak-to-peak 100 V in a frequency range of 1 to 10 MHz. Consequently, in order to switch the pulses of the positive and negative polarities having such high frequency and voltage, a high-voltage-rated switching element capable of conducting the pulse signal with both polarities is required for the switch $S_1$ to $S_n$. Such switching element or device may be realized in an arrangement shown in FIG. 3 in which diodes $D_1$ and $D_2$ are connected in an anti-parallel connection so as to pass and block the pulse signal of both polarities. With such circuit arrangement, however, a control circuit of a complicated configuration is required for applying high control voltages $V_a$ and $V_b$ of positive and negative polarities to the control terminals $T_1$ and $T_2$ of the diodes $D_1$ and $D_2$, respectively, and vice versa. Further, the signal passing through the switching element of this type will disadvantageously be subjected to distortion upon transition of the polarity of the signal, i.e. in the vicinity of the time point at which one diode is turned off (or blocked) while the other is turned on (conductive). The disadvantage of this kind will further be described below by referring to FIGS. 4a–4c.

In FIG. 4b there is shown a circuit in which the switching element is constituted by a conventional diode D which is conductive only in one direction. When the control voltage $V_c$ applied to the diode D through a terminal T is sufficiently lower than a minimum value $-V_x$ of an input pulse signal shown in FIG. 4a, the diode functions to block the input pulse voltage. In other words, the switching element is in the blocked or non-conducting state. On the other hand, when the control voltage $V_c$ is higher than the peak voltage $V_p$ of the input pulse signal, the latter can pass through the diode D. In other words, the diode switch is in the conducting state. Accordingly, in the case of the switch circuit shown in FIG. 4b, the control voltage has to be higher than the highest level of the input pulse signal and lower than the lowest level thereof. To this end, a control voltage having a large amplitude in both positive and negative regions is required, involving a complicated control circuit and thus making impractical the switching circuit shown in FIG. 4b. It should additionally be mentioned that when the control voltage $V_c$ is of a single polarity, e.g. varies between zero and the level $-V_x$, the output voltage from the switching circuit exhibits a rectified waveform corresponding to the input pulse voltage having the positive amplitude range blocked, as shown in FIG. 4c.

SUMMARY OF THE INVENTION

An object of the present invention is to provide a switching circuit for exciting ultrasonic transducer elements which circuit is capable of transmitting exciting pulses for the transducer element without distortion in a simplified circuit configuration.

In view of the above object, it is proposed according to an aspect of the invention that a diode exhibiting a long reverse recovery time is used as the switching element for constituting the switch circuit for excitation of the ultrasonic transducer elements.

The above and other objects, features and advantages of the present invention will become more apparent from the following description of the preferred embodiments of the invention. The description makes reference to the accompanying drawings.

BRIEF DESCRIPTION OF THE DRAWINGS

FIG. 3 is a circuit diagram showing a switching element for a bipolar signal.

FIGS. 4a-4c are to illustrate operation characteristics of a conventional switching diode.

FIG. 5 shows a structure of a diode employed in accordance with the invention.

FIG. 6 shows graphically a characteristic of a diode having a structure shown in FIG. 5.

DESCRIPTION OF THE PREFERRED EMBODIMENTS

In the first place, a switching element employed in the ultrasonic transducer exciting circuit according to the invention will be described.

According to the teaching of the invention, a diode exhibiting a long reverse recovery time i.e. the diode exhibiting a significant hole storage effect is made use of as the switching element to be employed in the exciting circuit. With the expression "hole storage effect", it is intended to mean such a phenomenon of a diode in which a backward or reverse current will flow when the diode operating in the forward direction is abruptly biased in the backward direction. Usually, such hole storage phenomenon is undesirable. To this end, the hole storage effect of diode is suppressed by diffusing gold in the impurity-doped layer of the diode or resorting to other means. In contrast, according to the teaching of the invention, the hole storage effect is positively utilized, thereby to cause the diode to operate transiently or momentarily as the bipolar switching element. In particular, the hole storage phenomenon can be advantageously and effectively utilized for processing the pulse signal for exciting the ultrasonic transducer element, since such pulse signal is in the form of a burst wave having a duration of the order of several microseconds. Accordingly, the diode which exhibits more significant hole storage effect is more preferably employed.

A typical one of the diodes having the characteristic described above is commercially available from Hitachi Limited in Japan as Type ISS122. The diode is of such a structure as shown in FIG. 5. Referring to the figure, the diode has a thin N-type epitaxial layer ($N^-$-EP) formed on a N-type silicon substrate $N^+$ through epitaxial growth and having a high impurity concentration. A P-type layer P is formed on the layer $N^-$-EP through diffusion. Electrodes Au of gold are deposited on the top and the bottom face of the diode for ohmic contact.

Figure 1:
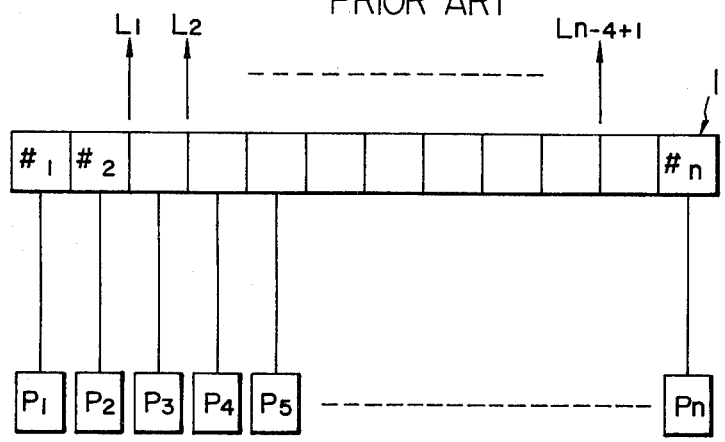
FIG. 1 illustrates schematically a principle of a hitherto known ultrasonic transducer array device of electronic linear scan type.
Figure 2:
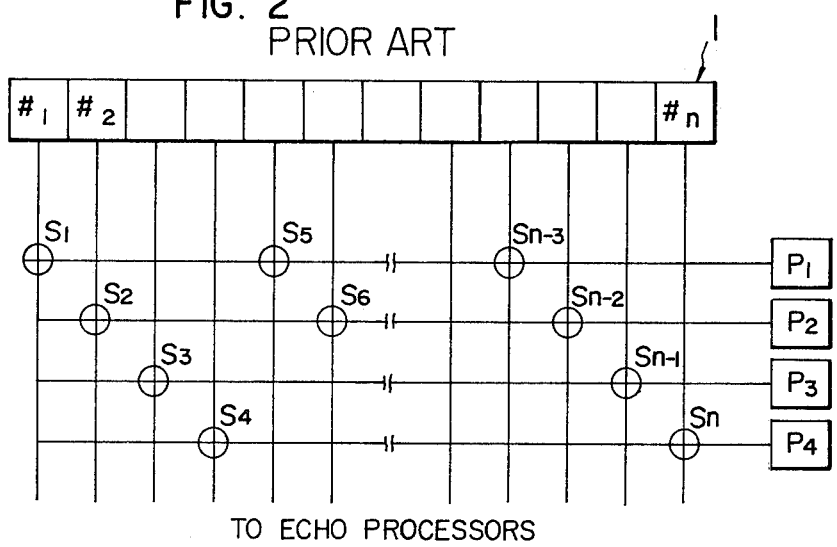
FIG. 2 shows schematically a conventional switch circuit for exciting the ultrasonic transducer array.
Figures 7A, 7B, 7C:
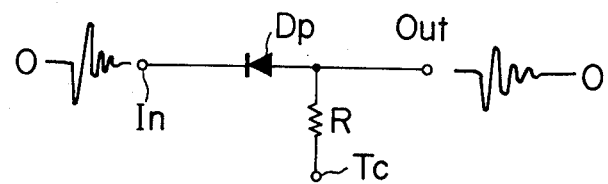
FIGS. 7a-7c are to illustrate an embodiment of the invention.

FIG. 7b shows a circuit arrangement of a switching element used in the exciting circuit according to an embodiment of the invention. The circuit includes a diode $D_p$ having a characteristic shown in FIG. 6 and exhibiting a long reverse recovery time (of the order of 10 $\mu$sec, for example) and a resistor element R connected to the diode $D_p$. In FIG. 7b, symbol $I_n$ represents an input terminal, $O_{ut}$ represents an output terminal and $T_c$ represents a control terminal.

With the arrangement shown in FIG. 7b, when a bipolar pulse signal having a duration of several microseconds as shown in FIG. 7a is applied to the input terminal $I_n$ as the input voltage, a bipolar pulse voltage shown in FIG. 7c can be obtained as the output voltage from the output terminal $O_{ut}$. The control terminal $T_c$ is supplied with a positive voltage which is lower than the input voltage. In conjunction with the connection of the diode $D_p$ shown in FIG. 7b, the rise-up direction of the input voltage pulse shown in FIG. 7a is so selected as to bias forwardly the diode $D_p$. However, it will be readily understood that the rise-up direction of the input voltage pulse is reversed when the diode $D_p$ is connected with the polarity opposite to the one shown in FIG. 7b.

Figure 8:
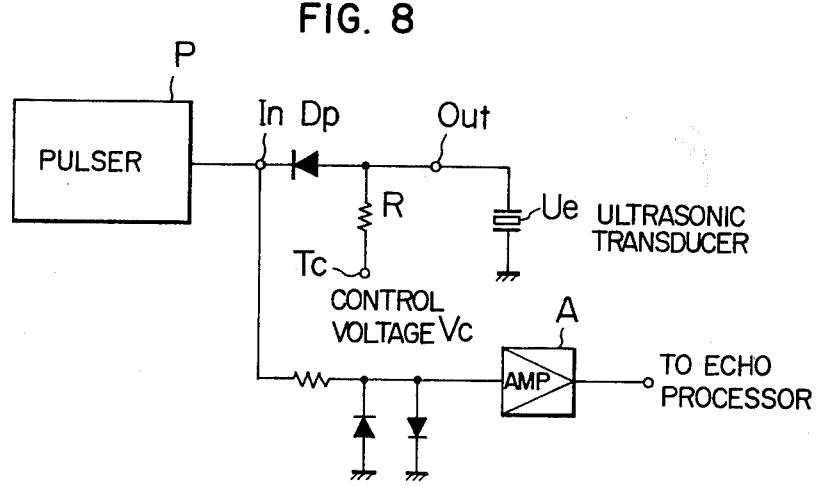
FIG. 8 shows a circuit arrangement of an ultrasonic diagnostic apparatus to which the invention is applied.

FIG. 8 shows an ultrasonic diagnostic apparatus to which the invention is applied and in which reflected echo is received for being processed for diagnosis by changing over the ultrasonic wave transmission mode to the echo reception mode. Referring to the figure, the diode $D_p$ is in the OFF-state (i.e. non-conducting or blocked state) so long as the control voltage $V_c$ of the diode $D_p$ is sufficiently lower than the pulse voltage generated by the pulser P. When the control voltage $V_c$ is low in the positive region, the pulse signal for causing the ultrasonic wave to be transmitted is applied to the ultrasonic transducer element $U_e$. In other words, the diode $D_p$ becomes momentarily conductive in both directions to allow the output burst signal to pass therethrough, resulting in generation of the ultrasonic wave from the transducer element $U_e$. The ultrasonic wave reflected as an echo from an object to be examined is received and converted into a voltage signal of very small magnitude by the transducer element $U_e$ through piezo-electric conversion. The echo signal is then supplied to an amplifier A after passing through the diode $D_p$ since the control voltage $V_c$ is a positive voltage of the order of several volts. In this manner, the signal to be transmitted as well as the received signal can be changed over to each other through the diode $D_p$.

As will be appreciated from the foregoing description, the invention has provided an advantageous switching circuit for both of the signal to be transmitted to the ultrasonic transducer element for emission of the ultrasonic wave and the echo signal received by the element to be supplied to a processing system by using diodes exhibiting a long reverse recovery time. In the foregoing description, it has been assumed that the diode of the specified characteristic is used. However, it goes without saying that other semiconductor elements exhibiting the reverse recovery time of a considerable duration such as silicon controlled rectifiers (SCR) can be employed to the similar effect.

We claim:

1. A switch circuit for an ultrasonic transducer element comprising a diode having a cathode connected to an input terminal for pulse signals for exciting the ultrasonic transducer element and an anode connected to an output terminal, said anode also being connected through a resistor to a control voltage terminal for controlling a conductive state of said diode, said diode having a long reverse recovery time due to a hole storage effect and being adapted to produce pulse signals having bipolar pulse components at the output terminal in accordance with the pulse signals at the input terminal.

2. A switch circuit according to claim 1, wherein said diode has a reverse recovery time of several microseconds.

3. A switch circuit according to claim 1 or 2, wherein said diode has a reverse recovery time of about 10 microseconds.

4. An apparatus for transmitting and receiving ultrasonic waves comprising at least one pulser means for generating pulses, at least one ultrasonic transducer means for transmitting ultrasonic waves and receiving an echo from an object to produce echo signals, and switch circuit means having an input terminal connected to said pulser means and an output terminal connected to said ultrasonic transducer means for applying pulse signals to said ultrasonic transducer means and passing the received echo signals to an echo processor means connected to a connecting point at which said pulser means is connected to said input terminal of said switch circuit means, said switch circuit means comprising a diode having a cathode connected to said input terminal and an anode connected to said output terminal, said anode also being connected through a resistor to a control voltage terminal means for controlling a conductive state of said diode, said diode having a long reverse recovery time due to a hole storage effect and being adapted to produce pulse signals having bipolar pulse components at said output terminal in accordance with pulses of said pulser means.

5. An apparatus according to claim 4, wherein said diode of said switch circuit means passes the received echo signals to said echo processor means.

6. An apparatus according to claim 4, wherein said diode has a reverse recovery time of several microseconds.

7. An apparatus according to claim 6, wherein said diode has a reverse recovery time of about 10 microseconds.

8. An apparatus according to claim 4, wherein a plurality of ultrasonic transducer means and switch circuit means are provided, a respective switch circuit means being interposed between the at least one pulser means and an associated ultrasonic transducer means.

9. An apparatus according to claim 8, wherein a plurality of pulser means are provided, a respective switch circuit means being interposed between a respective pulser means and an associated ultrasonic transducer means.

* * * * *